United States Patent [19]

Ghilardi et al.

[11] 3,981,678

[45] Sept. 21, 1976

[54] LYOPHILIZED DYES AND THE USE THEREOF TO COLOR KERATINIC FIBERS

[75] Inventors: Giuliana Ghilardi, Paris; Pierre Boré, Montfermeil; Jean-Francois Grollier, Paris, all of France

[73] Assignee: L'Oreal, Paris, France

[22] Filed: June 25, 1973

[21] Appl. No.: 372,934

Related U.S. Application Data

[63] Continuation-in-part of Ser. No. 120,353, March 2, 1971, abandoned.

[30] Foreign Application Priority Data

| Mar. 3, 1970 | Luxemburg | 60449 |
| Oct. 19, 1970 | Luxemburg | 61890 |
| Feb. 15, 1971 | Luxemburg | 62596 |
| June 26, 1972 | Luxemburg | 65590 |

[52] U.S. Cl............................. 8/11; 8/10; 8/10.1; 8/10.2; 8/19; 8/25; 8/32; 8/79; 8/93
[51] Int. Cl.$^2$................................. A61K 7/12
[58] Field of Search............... 8/10, 10.1, 11, 10.2, 8/79, 85, 93, 19, 32, 25; 260/396 R, 396 N

[56] References Cited

UNITED STATES PATENTS

| 3,402,986 | 9/1968 | Zviak et al. | 8/10 |
| 3,583,877 | 6/1971 | Rosenblum et al. | 8/79 |
| 3,698,852 | 10/1972 | Pantzer et al. | 8/10.2 |
| 3,712,790 | 1/1973 | Kalopissis et al. | 8/11 |
| 3,730,677 | 5/1973 | Kalopissis et al. | 8/11 |
| 3,758,268 | 9/1973 | Kalopissis et al. | 8/11 |
| 3,787,174 | 1/1974 | Kalopissis et al. | 8/11 |
| 3,867,094 | 2/1975 | Kalopissis et al. | 8/10 |
| 3,876,368 | 4/1975 | Kalopissis et al. | 8/10 |
| 3,884,625 | 5/1975 | Kalopissis et al. | 8/10 |
| 3,899,288 | 8/1975 | Galerne | 8/10.2 |
| 3,905,761 | 9/1975 | Kalopissis et al. | 8/10.2 |
| 3,929,403 | 12/1975 | Kalopissis et al. | 8/10.1 |

FOREIGN PATENTS OR APPLICATIONS

| 1,492,121 | 6/1969 | Germany | 8/11 |
| 826,479 | 1/1960 | United Kingdom | 8/10.1 |
| 807,089 | 1/1959 | United Kingdom | 8/79 |

OTHER PUBLICATIONS

P–Benzoquinonediimine — A Vital Intermediate in Oxidative Hair Dyeing, J. F. Corbett, J. Soc. Cosmetic Chemists, vol. 20, No. 4, pp. 253–263 (Apr. 1969).

*Primary Examiner*—Benjamin R. Padgett
*Assistant Examiner*—T. S. Gron
*Attorney, Agent, or Firm*—Cushman, Darby & Cushman

[57] ABSTRACT

A process for producing a dye in powder form involves reacting an oxidation agent with an oxidation base in an aqueous alkaline medium, preferably an ammoniacal medium, having a pH ranging from 8 to 13, in the presence of an organic solvent for the dye being produced, at a temperature and during a period of time allowing at least a partial oxidation, preferably between 15°–30°C for a period of about 5 minutes to 30 hours and lyophilizing the resulting reaction product. The resulting dye can be used to color keratinic fibers, especially human hair.

9 Claims, No Drawings

LYOPHILIZED DYES AND THE USE THEREOF TO COLOR KERATINIC FIBERS

This application is a continuation-in-part of our application Ser. No. 120,353 filed Mar. 2, 1971, now abandoned.

The present invention relates to a process for dyeing keratinic fibers and in particular human hair, according to which the dyeing is effected with the aid of a dye composition obtained by dissolving or dispersing in a cosmetic vehicle a powder prepared by the lyophilization of a solution including the reaction mixture obtained by the action of an oxidizing agent such as $H_2O_2$ in an alkaline medium, preferably an ammoniacal medium, on one or more oxidation bases, i.e. precursors of oxidation dyes, optionally in the presence of one or more couplers for the oxidation base, in amounts which can be equimolar although non-equimolar amounts of each can be employed.

The invention is also concerned with a lyophilized powder or lyophilized dye employed in said dyeing operation, with the process of preparing the same and with the dye compositions prepared from said lyophilizates.

The present invention is concerned particularly with a dye powder which includes said dye lyophilizates as well as to a hair dye composition obtained by dissolving or dispersing the said dye powder in a cosmetic vehicle. The present invention further relates to the use of such dye compositions for dyeing keratinic fibers, particularly, human hair.

In accordance with the present invention, the process of lyophilization is carried out so as to obtain a dye lyophilizate by initially reacting an oxidizing agent, such as $H_2O_2$, with one or more oxidation bases, the molar ratio of oxidizing agent to oxidation base ranging between about 0.1:1 to 20:1, in order to produce at least partial oxidation of the said oxidation base. Preferably, an excess of oxidizing agent is employed. Further, the reaction is effected in an aqueous solution containing one or more organic solvents. The resulting reaction medium, after having eliminated any excess oxidizing agent, is lyophilized by freezing the same at a temperature ranging from about −60° to −200°C, generally from −60° to −90°C, thereby terminating the reaction and subliming said reaction mixture or medium at a temperature of about −30° to −50°C, preferably below −35°C at a pressure of about 0.1 to 0.01 mm Hg. The step of freezing the reaction mixture, of course, can be implemented at any desired stage of the reaction, the process of which can be followed by chromatographic analysis. Following lyophilization, if desired or necessary to eliminate any residual moisture content, the lyophilized dye can be desorbed at a temperature ranging from between 15° to 60°C, at a pressure ranging between 10 mm to 0.001 mm Hg, preferably about 0.01 mm Hg.

The organic solvent utilized can be any one of tertiobutyl alcohol, dimethylsulfoxide, dioxane or benzyl alcohol and can be employed as an aqueous mixture thereof wherein water can be present in amounts of about 0–95 weight percent of the mixture. Generally the organic solvent is present in amounts of about 5 to 75 percent by weight of the reaction mixture.

The oxidation bases used in the process of the present invention are those generally employed in dyeing processes employing oxidation dyes. Representative oxidation bases include those listed in the Colour Index, 2nd edition, 1956, Vol. 3, pages 3593–3601. For example, the following bases can be employed: paratoluylene diamine, paraphenylene diamine, N,N-dimethyl paraphenylene diamine, methyl paraphenylene diamine, chloroparaphenylene diamine, 2-methoxy-5-methyl paraphenylene diamine, 2,6-dimethyl-3-methoxy paraphenylene diamine, tetramethyl paraphenylene diamine, 2-methoxy paraphenylene diamine, paraaminophenol, 2,6-dimethyl paraaminophenol, 2,4-diamino anisole, 2-methyl paraaminophenol and 1-methoxy-2,5-dimethyl paraphenylene diamine.

As indicated above, the reaction can optionally be carried out in the presence of one or more coupling agents, the molar ratio of coupling agent to oxidation base being between about 0:1 to 10:1 and preferably between 0:1 to 2:1.

Representative couplers utilized in the process of the present invention are those generally employed in dye processes using oxidation dyes and can include for example: metaphenylene diamine, 2,4-diamino anisole, 2,4-diamino toluene, metaaminophenol, 6-methyl-3-amino phenol, N-methyl metaaminophenol, 4-methoxy-3-amino phenol, resorcinol, 2,6-xylenol and α-napthol. It should be noted that 2,4-diamino anisole which is a metadiamine and therefore has the structure of a coupler, can, in certain instances and in particular when it is used alone, be employed as a base.

There can be added to the reaction mixture as fillers, oligopeptides such as hydrolysis products of proteins, amino acids, polymers such as polyvinylpyrrolidone (PVP) having a molecular weight ranging between 40,000 to 360,000, the preferred molecular weight being 40,000 or copolymers such as the copolymer of polyvinylpyrrolidone and vinyl acetate (MW = 40,000-160,000) 70% : 30% to 30% : 70%, the preferred proportion being 60% : 40%, having a viscosity of 3.3 to 4cp (at 25°C) in 5% solution in ethanol, or copolymers of crotonic acid and vinyl acetate, 90% : 10% having a molecular weight of 40,000 to 200,000 and preferably of 50,000 and a viscosity of 7 to 9 cp (at 35°) in 5% solution in tetrachloroethane. This addition has the effect of increasing the total volume and ensuring a very high degree of reproducibility of the characteristics of the lyophilizate obtained and of its dyeing properties. Generally, to total amount of filler employed will range between 1 to 20 and preferably 5, weight percent of the total reaction mixture.

Representative protein hydrolysis products include such products as those known under the commercial designations: "Keratin Hydrolyzate" by GEO; "Complex Aminoacid" by GEO; "Casein Hydrolyzate" by GEO; "Capilane KS" by Sandoz; "Polypeptide Wilson W.S. P. 250" and "Polypeptide L.S.N." by Stopan Chemicals.

Representative amino acids include alanine, glycine, glutamic acid and cystine.

The preparation of the lyophilizate is carried out in the following manner.

An aqueous alkaline solution, for example an ammoniacal solution is prepared containing an oxidation base and optionally one or more couplers, the solution having a pH greater than about 8 and generally between about 8–13. To this solution there is added one of the aforementioned organic solvents and an excess of $H_2O_2$. The resulting reaction mixture is then left to stand in open air, i.e. open to ambient atmosphere, at a temperature and for a time to permit at least a partial oxidation of the mixture. Generally the oxidation is carried out at a temperature between 15° and 30°C. The time required for the desired oxidation of the mixture can vary between about 5 minutes to several hours, for instance, 30 hours. The progression of the reaction can be followed by chromatographic analysis. The reaction can be stopped at the desired stage, by freezing at a temperature equal or lower than −60°C and one lyophilizes the reaction mixture thus obtained employing conventional lyophilization conditions which include sublimation and optionally a desorption operation. conveniently, the frozen mixture is sublimated in a conventional apparatus known as "USIFROID SMS" provided with an internal condenser although it will be appreciated that any conventional freezedrying means can be employed. As stated sublimation can be effected at a temperature lower than −30°C and preferably lower than −35°C under a pressure equal to or lower than 0.1 mm Hg.

When required, desorption can be effected at a temperature between 15° and 60°C under a very low pressure, generally in the order of about 0.005 to 0.01 mm Hg, the temperature of the condenser in the apparatus employed being maintained at about −200°C. The total duration of lyophilization under these conditions is of the order of abut 10–30 hours, usually about 20 hours. The lyophilized product thus obtained is a powder exhibiting a very high specific surface area.

In another embodiment of the present invention the ammonia and/or the excess $H_2O_2$ can be eliminated from the reaction mixture prior to freezing the same. $H_2O_2$ can be eliminated by the addition of potassium permanganate in amounts effective to precipitate the manganese dioxide which forms therein.

As indicated above, the reaction can be stopped either when the oxidation of the mixture has completely run its course or at an intermediate stage, in a manner such that the lyophilizate obtained contains a certain quantity of oxidation base and optionally of coupler. In this case, a lyophilizate is obtained which can be used partially as a direct dye and partially as an oxidation dye, which permits the production of a substantial varied range of dye compositions.

The lyophilizates obtained constitute powders which can serve for the preparation of dye compositions.

These lyophilizates can be mixtures of other lyophilyzates or with atomizates, with resins, with optical brightening agents or with components generally employed in cosmetics such as thickening agents and/or acid dyes, basic dyes or direct dyes, soluble or dispersible, such as anthraquinone dyes, azo dyes, nitro dyes or complex metalliferous dyes, or even indamines, indoanilines and indophenols.

Representative indamines, indoanilines and indophenols can be combined with the lyophilized dye of this invention and can have the formula.

$$Y - Ar_1 - N = Ar_2 = X \qquad (I)$$

or a corresponding tautomeric form thereof wherein $Ar_1$ and $Ar_2$, each independently represent aromatic hydrocarbon or heterocyclic nucleus, each optionally substituted by one or more electron donor groups such as amino, hydroxy, lower alkoxy, lower alkyl, acylamino or halogen such as chlorine or bromine, Y represents hydroxy or

wherein $R_1$ and $R_2$, each independently represent hydrogen, lower alkyl, hydroxy lower alkyl or amino lower alkyl with the amino function optionally being substituted or acylated and X represents oxygen or imine or iminium, or a salt of these compounds.

It is convenient to note that the nomenclature adopted for these compounds corresponds to a numbering of the aromatic rings $Ar_1$ and $Ar_2$ which, is as follows:

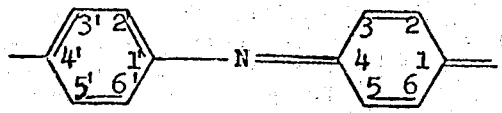

Representative indamines usefully employed in the process of the present invention include N-[(4'-dimethylamino) phenyl]-3-amino-6-methyl benzoquinonediimine hydrochloride, N-[(4'-amino-2'-methoxy-5'-methyl)phenyl]-2-aza-3-amino benzoquinonediimine monoacetate, the double chloride of zinc and N-[(ethyl acetylaminoethyl)-4'-amino phenyl]-3-amino-6-methoxy benzoquinonediimine, N-[(4'-amino-2'-methoxy-5'-methyl)phenyl]- 3-amino-6-methyl benzoquinonediimine monoacetate and the double chloride of zinc and N-[(ethyl β-acetylaminoethyl)-4'-amino phenyl]-3-hydroxy benzoquinone N',-N'-diethyliminium.

Representative indoanilines usefully employed in the process of the present invention include N-[(4'-dimethylamino) phenyl]-2,6-dimethyl benzoquinoneimine, N-[(4'-dimethylamino) phenyl]-2,5-dimethyl benzoquinoneimine, N-[(4'-amino-2'-methoxy-3',5'-dimethyl)phenyl]-2,6-dimethyl benzoquinoneimine, N-[(4'-amino-2'-methoxy-3',5'-dimethyl)phenyl]-2,5-dimethyl benzoquinoneimine, N-[(4'-dimethylamino)-phenyl]-3-amino-6-methyl benzoquinoneimine, N-[(4'-amino-2'-methoxy)phenyl]-3-amino-6-methyl benzoquinoneimine, N-[(4'-amino-2'-methoxy-5'-methyl)phenyl]-3-acetylamino-6-methyl benzoquinoneimine, N-[(4'-hydroxy)phenyl] -3-amino-6-methoxy benzoquinone diimine and N-[(4'-amino-3'-chloro)phenyl]-3-amino-2,6-dimethyl benzoquinoneimine.

Representative indophenols usefully employed in the process of this invention include N-[(4'-hydroxy)-phenyl]-2,6-dimethyl benzoquinoneimine, N-[(4'-hydroxy)phenyl]-2,5-dimethyl benzoquinoneimine, N-[(4'-hydroxy)phenyl]-3-amino-6-methyl benzoquinoneimine and N-[(4'-hydroxy-3',5'-dimethyl)-phenyl]-2,6-dimethyl benzoquinoneimine. Other indophenols, indamines and indoanilines suitably employed are those disclosed in commonly assigned U.S. Patent applications Ser. No. 45,564, filed June 11, 1970, now abandoned, Ser. No. 49,905, filed June 25, 1970, now abandoned, Ser. No. 52,739, filed July 6, 1970, now U.S. Pat. No. 3,677,690, Ser. No. 97,395, CIP of Ser. No. 45,564, filed Dec. 11, 21, 1970, now abandoned, Ser. No. 100,433, CIP of Ser. No. 49,905 filed Dec. 21, 1970, now abandoned, and Ser. No. 161,887, CIP of Ser. No. 52,739, filed July 12, 1971, now U.S. Pat. No. 3,758,268. Generally the amount of indophenol, indoaniline or indamine added to the dye composition will range between about 1 to 99 weight percent of the total weight of the powder.

The powders containing the lyophilizate, alone or in admixture with other adjuvants and/or other dyes, can be compressed into tablet or pill form and can be employed to prepare hair dye solutions or dispersions.

The lyophilizate can be added to an appropriate cosmetic vehicle containing adjuvants such as cosmetic resins, thickeners, solar filters, perfumes, optical bleaching agents and/or other components conventionally employed in cosmetics.

The present invention also relates to dye compositions comprising the said lyophilizates or powders containing the said lyophilizates in admixture with adjuvants and/or other dyes. The pH of these compositions is generally between about 2.5–10, the desired pH being obtained most often by the addition of a suitable quantity of a mineral or organic base such as triethanolamine or ammonia or of a suitable quantity of an acidic material such as lactic or citric acid. Obviously other conventional substances normally used to adjust the pH of cosmetic preparations can also be used.

The dye compositions prepared with the dyes of the present invention can also be employed as a "bleaching dye" composition, when used in the presence of $H_2O_2$ in an ammoniacal medium. Such a "bleaching dye" composition has a pH ranging from about 8–12. The dyes of this invention can also be employed to produce a "tinting" dye composition by including therein an oxidation dye or base as defined above. Generally the oxidation dye or base will be present in amounts ranging from about 0.05 to 4 percent by weight of the total composition.

The compositions of the present invention include from 0.0005 to 5% by weight of the lyophilized dye.

They can be present in the form of an aqueous or hydroalcoholic solution, a gel or a cream. In producing the hydroalcoholic solution there is generally employed a lower alkanol such as ethanol or isopropanol present in amounts of about 1 to 96 weight percent of the resulting aqueous alkanol solution. These compositions can also be packaged in an aerosol container, a dosage bottle or in a container for several components or in a container for the mixture before use.

The dye compositions can also include an alcohol generally a lower alkanol such as ethanol or isopropanol and one or more cosmetic resins to provide a colored hair setting lotion.

Representative cosmetic resins that can be employed in the dye compositions can include, for instance, polyvinylpyrrolidone having a molecular weight ranging from 40,000 to 360,000, a copolymer of vinylpyrrolidone and vinyl acetate having a molecular weight ranging from 40,000 to 160,00 (70%:30% to 30%:70%, respectively), a copolymer of crotonic acid and vinyl acetate (90:10) having a molecular weight ranging from 40,000 to 200,000 and mixtures thereof. Generally the cosmetic resin, when used, will be employed in amounts ranging from 0.5 to 4 weight percent of the dye composition.

The process of dyeing with dye compositions containing the lyophilized dyes of the present invention is effected in a very simple manner by applying the dye composition directly to the hair or other keratinic fiber, which application can optionally be followed by a washing and/or a rinsing operation.

Further, there can be added to the dye composition at the moment of use, $H_2O_2$, and the resulting composition can be applied to the hair for about 5–40 minutes after which the hair is rinsed, washed and dried.

It is also possible to use the dye compositions of the invention as a nonpermanent dye and in this case the hair is not subsequently washed thereby achieving a special dye effect.

The advantages obtained by the present invention include the following.

The use of an organic solvent in the preparation of the dye provides a homogeneous solution of the dye and thus renders more easy flexible and reproducible the subsequent lyophilization operation. Further the control of the stage or degree of oxidation is more easily effected by chromatography when using an organic solvent and the reaction mixture which is submitted to lyophilyzation is completely homogeneous, thereby assuring the attainment of lyophilizate particles having a very high specific area which provides a more rapid and complete solubilization of the lyophilizate in the cosmetic vehicle in the preparation of the dye compositions.

The powder obtained by lyophilization has a solubility in water generally greater than 5 g/liter and up to about 100g/liter or higher.

Further, the lyophilizate obtained is easily preserved for long periods without alteration which permits (1) its advantageous transformation into a dye composition just before its application to the hair, and (2) the attainment of a range of shades more varied and (3) a greater reproducibility of the colors obtained on hair. Moreover, the dyeings which are effected with a dye composition obtained with a lyophilizate containing the product of reaction of an oxidation base in the presence of specific couplers, and of which the application on the hair is made as with a direct dye, gives a quality result comparable to a dyeing made with a dye composition containing the same base and the same coupler in the same amounts, but wherein the application is made after the addition of ammonia and $H_2O_2$ to the dye composition. Thus the present invention permits the use of a mode of application applicable to a direct dye, to obtain a quality of dyeing comparable to that obtained with oxidation dyes without, however, the inconveniences of the latter. This feature is particularly important because oxidation dyes known prior to the present invention could not in any manner be adapted to this type of application to the hair.

The following examples illustrated the present invention.

EXAMPLE 1

There is left standing in open air at a temperature of about 15°C for 60 minutes in "penicillin" bottles at a depth of 7 mm the following solution:

| | |
|---|---|
| Paraaminophenol | 0.218 g (0.002 mole) |
| 2,4-diaminoanisole dihydrochloride | 0.422 g (0.002 mole) |
| Polyvinylpyrrolidone (MW = 40,000) | 5 g |
| Ammonia (20% solution) | 10 cc |
| Tertiobutyl alcohol | 50 g |
| $H_2O_2$ (30 volumes) | 26.6 g |
| Water, q.s.p. | 100 g |

After 30 minutes, there is added to the resulting reaction mixture a quantity of N/10 potassium permanganate sufficient to eliminate excess $H_2O_2$, by precipitating the manganese dioxide formed. The presence of the organic solvent prevents the precipitation of the dye obtained. The reaction mixture is filtered to remove the manganese dioxide and the resulting filtrate is frozen at −60°C for one hour in a lyophilizing apparatus called USIFROID at a temperature of −40°C and at a pressure of 0.05 mm Hg for 24 hours.

Desorption is effected at a temperature of +25°C.

The chromatography of the lyophilizate on a silica layer reveals no trace of either paraaminophenol or 2,4-diamino anisole dihydrochloride, but reveals, among others, the presence of the following dye:

N[(4'-hydroxy)phenyl]-3-amino-6-methoxy benzoquinonediimine, identical to that obtained by synthesis.

EXAMPLE 2

There is left standing in open air for 30 minutes at a temperature of about 20°C in "penicillin" bottles at a depth of 7 mm, the following solution;

| | |
|---|---|
| Paraphenylenediamine | 0.108 g (0.001 mole) |
| 2,6-xylenol | 0.122 g (0.001 mole) |
| Ammonia (20% solution) | 10 cc |
| Polyvinylpyrrolidone (MW 40,000) | 5 g |
| Dioxane | 40 g |
| $H_2O_2$ (30 volumes) | 26.6 g |
| Water, q.s.p. | 100 g |

After 30 minutes, there is added to the reaction mixture obtained, a quantity of N/10 potassium permanganate necessary to eliminate excess $H_2O_2$ by the precipitation of manganese dioxide. The dye formed is entirely dissolved in the organic solvent containing reaction solution. The said solution is then filtered to eliminate the manganese dioxide. The filtrate is then frozen in the penicillin type bottles at −60°C for 1 hour and then sublimated and desorbed as set forth in Example 1. The lyophilizate is in the form of tablets having a beautiful appearance.

The chromatography of the lyophilizate on a silica layer reveals, amongst others, the presence of the following indoaniline:

N-[(4'-amino)phenyl]-2,6-dimethyl benzoquinoneimine, identical to the synthesized product.

EXAMPLE 3

There is left standing in open air for 25 minutes at a temperature of about 25°C; in "penicillin" bottles at a depth of 7 mm the following solution:

| | |
|---|---|
| Paradiamino-2,4-dimethyl anisole dihydrochloride | 0.119 g (0.0005 mole) |
| 2,6-xylenol | 0.061 g (0.0005 mole) |
| Ammonia (20% solution) | 10 cc |
| Polyvinylpyrrolidone (MW = 40,000) | 5 g |
| Tertiobutyl alcohol | 25 g |
| $H_2O_2$ (30 volumes) | 26.6 g |
| Water, q.s.p. | 100 g |

After 30 minutes, there is added to the reaction mixture obtained, a quantity of N/10 potassium permanganate to eliminate excess $H_2O_2$ by precipitation of manganese dioxide. The dye formed is entirely dissolved in the organic solvent containing reaction solution. The solution is filtered to eliminate the manganese dioxide and the resulting filtrate is frozen in the penicillin type bottles at −60°C for 1 hour. The frozen filtrate is then sublimated and desorbed as in Example 1.

Chromatography of the lyophilizate on a layer of silica reveals some traces of 2,6-xylenol, while no trace of paradiamino-2,4-dimethyl anisole is observed. The said chromatography also reveals the presence of the following dye:

N-[(4'-amino-2'-methoxy-3',50'-dimethyl)phenyl]-2,6-dimethyl benzoquinoneimine.

EXAMPLE 4

There is left standing in open air for 30 minutes at a temperature of about 20°C in "penicillin" bottles at a depth of 7 mm the following solution:

| | |
|---|---|
| Paraaminophenol | 4.36 g (0.04 mole) |
| 2,4-diamino anisole dihydrochloride | 4.22 g (0.02 mole) |
| Polyvinylpyrrolidone (MW = 40,000) | 5 g |
| Ammonia (20% solution) | 10 cc |
| Tertiobutyl alcohol | 25 g |
| $H_2O_2$ (30 volumes) | 26.6 g |
| Water, q.s.p. | 100 g |

After 30 minutes, there is added to the reaction mixture obtained, a quantity of N/10 potassium permanganate sufficient to eliminate excess $H_2O_2$, by precipitation of the manganese dioxide formed. The presence of the organic solvent prevents the precipitation of the dye obtained. The solution is filtered to remove the manganese dioxide precipitate and the resulting filtrate is then frozen at −60°C for 1 hour after which it is subjected to the sublimation and desorption procedures outlined in Example 1.

The chromatography of the lyophilizate on a silica layer reveals no trace of either paraaminophenol or of 2,4-diamino anisole dihyrochloride, but it does reveal, amongst others, the presence of the following dye:

N-[(4'-hydroxy)phenyl]-3-amino-6-methoxy benzoquinonediimine, identical to that obtained by synthesis.

EXAMPLE 5

There is left standing in open air for 20 minutes at a temperature of about 30°C in "penicillin" bottles at a depth of 7 mm the following solution:

| | | |
|---|---|---|
| Paraaminophenol | 4.36 | g (0.04 mole) |
| 2,4-diamino anisole dihydrochloride | 4.22 | g (0.02 mole) |
| Polyvinylpyrrolidone (MW = 40,000) | 5 | g |
| Ammonia (20% solution) | 10 | cc |
| Tertiobutyl alcohol | 75 | g |
| $H_2O_2$, q.s.p. | 20 | volumes |
| Water, q.s.p. | 100 | g |

After 30 minutes, there is added to the reaction mixture obtained, a sufficient quantity of N/10 potassium permanganate necessary to eliminate excess $H_2O_2$, by the precipitation of the manganese dioxide formed.

The presence or the organic solvent prevents the precipitation of the dye obtained. The solution is filtered to remove the manganese dioxide precipitate and the resulting filtrate is frozen at −60°C for 1 hour after which it is subjected to the sublimation and desorption procedures set forth in Example 1.

Chromatography of the lyophilizate on a silica layer reveals no trace of either paraaminophenol or of 2,4-diamino anisole dihydrochloride, but it does reveal, amongst others, the presence of the following dye:

N[(4′-hydroxy)phenyl]-3-amino-6-methoxy benzoquinonediimine, identical to that obtained by synthesis.

EXAMPLE 6

There is left standing in open air for 30 minutes at a temperature of about 20°C in "penicillin" bottles at a depth of 7 mm the following solution:

| | |
|---|---|
| Paraphenylenediamine | 0.108 g (0.001 mole) |
| 2,6-xylenol | 0.122 g (0.001 mole) |
| Ammonia (20% solution) | 10 cc |
| Polyvinylpyrrolidone (MW = 40,000) | 5 g |
| Dioxane | 75 g |
| $H_2O_2$, q.s.p. | 20 volumes |
| Water, q.s.p. | 100 g |

After 30 minutes, there is added to the resulting reaction mixture a sufficient quantity of N/10 potassium permanganate necessary to eliminate the excess $H_2O_2$ by precipitation of manganese dioxide. The dye formed is entirely dissolved in the organic solvent containing reaction solution. The solution is then filtered to eliminate the manganese dioxide and the resulting filtrate is frozen in the penicillin type bottles at −60°C for 1 hour, after which it is subjected to the sublimation and desorption procedures set forth in Example 1. The lyophilizate is in the form of tablets having a beautiful appearance.

Chromatography of the lyophilizate on a silica layer reveals, amongst others, the presence of the following indoaniline:

N[(4′-amino)phenyl]-2,6-dimethyl benzoquinoneimine, identical to the synthesized product.

EXAMPLE 7

Example 1 is repeated except that the paraaminophenol is used in amounts of 0.01 mole, the 2,4-diamino anisole dihydrochloride is used in amounts of 0.02 mole and the organic solvent used in dimethyl sulfoxide.

EXAMPLE 8

Example 1 is repeated except that the base is replaced by 0.01 mole of paratoluylene diamine and the coupler is replaced by 2,4-diamine anisole sulfate in amounts of 0.005 mole.

EXAMPLE 9

Example 1 is repeated except that the base is replaced by 0.01 mole of paratoluylene diamine, the coupler is replaced by 0.01 mole of metaaminophenol and the organic solvent is replaced by benzyl alcohol.

EXAMPLE 10

Example 1 is repeated except that the base is replaced by 0.01 mole of paratoluylene diamine and the coupler is replaced by 0.01 mole of N-methyl metaaminophenol hydrobromide.

EXAMPLE 11

Example 1 is repeated except that the base is replaced by 0.02 mole of paratoluylene diamine and the coupler is replaced by 0.01 mole of 3-amino-4-methoxy phenol.

EXAMPLE 12

Example 1 is repeated except that the base is replaced by 0.01 mole of paratoluylene diamine, the coupler is replaced by 0.01 mole of resorcinol and the organic solvent is replaced by dimethyl sulfoxide.

EXAMPLE 13

Example 1 is repeated except that as the base is replaced by 0.01 mole of 1-methoxy-2,5-dimethyl paraphenylene diamine and the same coupler is employed in amounts of 0.01 mole.

EXAMPLE 14

Example 1 is repeated except that as the base there are employed 0.01 mole of paratoluylene diamine and 0.01 mole of paraaminophenol, and as the coupler there are employed 0.01 mole of 2,4-diamino anisole dihydrochloride, 0.01 mole of resorcinol and 0.01 mole of metaamino phenol.

EXAMPLE 15

Example 1 is repeated except that as the base there is employed 0.2 mole of paratoluylene diamine, as the coupler there are employed 0.1 mole of resorcinol and 0.05 mole of metaaminophenol; and as the organic solvent there is employed dimethyl sulfoxide.

EXAMPLE 16

Example 1 is repeated except that as the oxidation base and coupler there is employed 2,4-diamino anisole dihydrochloride in amounts of 0.02 mole.

EXAMPLES 17–25

The procedures outlined in Example 1 are repeated using in comparable amounts the following oxidation bases rather than the paraaminophenol disclosed therein: N,N-dimethyl paraphenylene diamine, methyl paraphenylene diamine, chloro paraphenylene diamine, 2-methoxy-5-methyl paraphenylene diamine, 2,6-dimethyl-3-methoxy paraphenylene diamine, tetramethyl paraphenylene diamine, 2-methoxy paraphenylene diamine, 2,6-dimethyl paraamino phenol and 2-methyl paraamino phenol.

EXAMPLE 26

A lyophilic product is prepared in the following manner: There is left standing in the open air at a temperature of 25°C for a period of 10 hours in "penicillin" type bottles filled to a depth of 7 mm, a mixture comprising 50 g of 20-volume hydrogen peroxide, and 0,61 g (0,005 moles) of paratoluylenediamine, 0,482 g (0,002 moles) of 2,4-diaminoanisole dichlorhydrate 2,5 g of Polyvinyl pyrrolidone, and 5 ml of ammonia (22° Be) in 25 g of tertiobutyl alcohol and in water q.s.p. 100 ml.

After 30 minutes; there is added to the resulting reaction mixture a quantity of N/10 potassium permanganate sufficient to eliminate excess $H_2O_2$, by precipitating the manganese dioxide formed. The presence of the organic solvent prevents the precipitation of the dye obtained. The reaction mixture is filtered to remove the manganese dioxide and the resulting filtrate is frozen at −60°C for 1 hour in a lyophilizing apparatus called USIFROID at a temperature of −40°C and at a pressure of 0.05 mm Hg for 24 hours.

Desorption is effected at a temperature of +25°C.

EXAMPLES OF USING LYOPHILIZED DYES

EXAMPLE 27

A dye composition is prepared by mixing at the time of use 0.100 g of powder $P_1$ and 25 ml of a solution. $S_1$ defined below

| Powder $P_1$ | |
|---|---|
| Spray preparation as in Example 1 | |
| Solution $S_1$ | |
| Copolymer of crotonic acid and vinyl acetate 90:10 (MW 50.000) | 2 g |
| Ethyl alcohol | 20 g |
| Carbopol 940 (carboxybinyl polymer, carboxypolymethylene) sold by B.F. GOODRICH | 0.4 g |
| Triethanolamine | 0.8 g |
| Water, q.s.p. | 100 g |

This hair setting lotion which is a gel is applied on hair that has been bleached and dyed golden blond. After drying, the hair has a very handsome pearly rose blond hue

EXAMPLE 28

The following dye composition is prepared:

| Colored product of lyophilization prepared as in Example 26 | 0.1 g |
|---|---|
| "Ethomeen C" (condensation product of 5 molecules ethylene oxide on coconut amine) sold by Armour | 0.15 g |
| Triethanolamine, q.s.p. | pH 7 |
| Water, q.s.p. | 100 g |

Twenty cc of this lotion are applied to bleached hair and left in contact therewith for 20 minutes. Thereafter, the hair is washed and dried and then set and dried.

The hair thus treated is brilliant, easy to comb and dryed rosy beige.

What is claimed is:

1. A process for producing a lyophilized dyestuff for coloring keratinic fibers consisting essentially of reacting hydrogen peroxide with an oxidation base in an aqueous alkaline solution open to ambient atmosphere in the presence of an organic solvent for the resulting dyestuff, said organic solvent being selected from the group consisting of tert-butyl alcohol, dimethylsulfoxide, dioxane and benzyl alcohol and having a pH ranging from 8 to 13 at a temperature between about 15°–30°C for a period of about 5 minutes to 30 hours and lyophilizing said reaction mixture, the molar raito of said hydrogen peroxide to said oxidation base being between about 0.1:1 to 20:1, said oxidation base being selected from the group consisting of paratoluylene diamine, paraphenylene diamine, N,N-dimethyl-paraphenylene diamine, methyl paraphenylene diamine, chloroparaphenylene diamine, 2-methoxy-5-methyl paraphenylene diamine, 2,6-dimethyl-3-methoxy paraphenylene diamine, tetramethyl paraphenylene diamine, 2-methoxy paraphenylene diamine, para aminophenol, 2,6-dimethyl para aminophenol, 2,4-diamino anisole, 2-methyl para aminophenol, 1-methoxy-2,5-dimethyl paraphenylene diamine, and the hydrochlorides thereof, wherein lyophilizing said reaction mixture comprises freezing said reaction mixture at a temperature of about −200° to −60°C and subliming said frozen mixture at a temperature of about −50°C to −30°C at a pressure of about 0.01 mm Hg to 0.1 mm Hg.

2. The process of claim 1 which also includes desorbing the lyophilized reaction product at a temperature ranging between 15°–60°C at a pressure of about 0.01 mm Hg.

3. The process of claim 1 wherein said aqueous alkaline solution in an aqueous ammoniacal solution.

4. The process of claim 1 wherein said oxidizing agent and said oxidation base are reacted in the presence of filler selected from the group consisting of oligopeptide, amino acid, polyvinylpyrrolidone having a molecular weight ranging between 40,000 to 360,000, a copolymer of vinylpyrrolidone and vinyl acetate having a molecular weight ranging between 40,000 to 160,000 wherein the weight ratio of vinylpyrrolidone to vinyl acetate is 70%:30% to 30%:70% and a copolymer of crotonic acid and vinyl acetate having a molecular weight of 40,000 to 200,000 wherein the weight ratio of crotonic acid to vinyl acetate is 90%:10%, said filler being present in amounts of 1–20 percent by weight of the total reaction mixture.

5. The process of claim 4 wherein said filler is an amino acid selected from the group consisting of alanine, glycine, glutamic acid and cystine.

6. The process of claim 1 wherein said organic sovent is present in amounts of about 5 to 75 percent by weight of the reaction mixture.

7. A dye in powder form made in accordance with the process of claim 1.

8. A process for producing a lyophilized dyestuff for coloring keratinic fibers consisting essentially of reacting hydrogen peroxide with an oxidation base in an aqueous alkaline solution open to ambient atmosphere in the presence of a coupler selected from the group consisting of metaphenylene diamine, 2,4-diamino anisole, 2,4-diamino toluene, metaaminophenol, 6-methyl-3-aminophenol, N-methyl metaaminophenol, 4-methoxy-3-aminophenol, resorcin, 2,6-xylenol, α-naphthol, 3-methoxy-4-aminophenol and the sulfate, hydrochloride and hydrobromide thereof, the molar ratio of said coupling agent to said oxidation base before oxidation being between 0:1 and 10:1 and in the presence of an organic solvent for the resulting dyestuff, said organic solvent being selected from the group consisting of tert-butyl alcohol, dimethyl sulfoxide, dioxane and benzyl alcohol and having a pH ranging from 8 to 13 at a temperature between about 15°–30°C for a period of about 5 minutes to 30 hours and lyophilizing said reaction mixture, the molar ratio of said hydrogen peroxide to said oxidation base being between about 0.1:1 to 20:1, said oxidation base being selected from the group consisting of paratoluylene diamine, paraphenylene diamine, N,N-dimethyl paraphenylene diamine, methyl paraphenylene diamine, chloroparaphenylene diamine, 2-methoxy-5- methyl paraphenylene diamine, 2,6-dimethyl-3-methoxy paraphenylene diamine, tetramethyl paraphenylene diamine, 2-methoxy paraphenylene diamine, para aminophenol, 2,6-dimethyl para aminophenol, 2,4-diamino anisole, 2-methyl para aminophenol, 1-methoxy-2,5-dimethyl paraphenylene diamine and the hydrochlorides thereof, wherein lyophilizing said reaction mixture comprises freezing said reaction mixture at a temperature of about −200° to −60°C and subliming said frozen mixture at a temperature of about −50° to −30°C at a pressure of about 0.01 to 0.1 mm Hg.

9. The process of claim 8 wherein the molar ratio of said coupling agent to said oxidation base before oxidation is between 0:1 to 2:1.

* * * * *